(12) United States Patent
Vestgaarden

(10) Patent No.: US 9,375,243 B1
(45) Date of Patent: *Jun. 28, 2016

(54) METHOD FOR DEPLOYING A FUSION DEVICE FOR SACROILIAC JOINT FUSION

(71) Applicant: VG Innovations, LLC, St. Petersburg, FL (US)

(72) Inventor: Tov Inge Vestgaarden, St. Petersburg, FL (US)

(73) Assignee: VGI Medical, LLC, St. Petersburg, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 14/537,327

(22) Filed: Nov. 10, 2014

Related U.S. Application Data

(63) Continuation of application No. 13/625,180, filed on Sep. 24, 2012, now Pat. No. 8,882,818.

(51) Int. Cl.
| | |
|---|---|
| A61B 17/17 | (2006.01) |
| A61B 17/56 | (2006.01) |
| A61B 17/88 | (2006.01) |
| A61B 17/70 | (2006.01) |
| A61B 17/16 | (2006.01) |
| A61B 17/02 | (2006.01) |
| A61B 17/84 | (2006.01) |

(52) U.S. Cl.
CPC .......... *A61B 17/8805* (2013.01); *A61B 17/025* (2013.01); *A61B 17/1604* (2013.01); *A61B 17/1615* (2013.01); *A61B 17/1662* (2013.01); *A61B 17/1739* (2013.01); *A61B 17/7074* (2013.01); *A61B 17/846* (2013.01); *A61B 2017/0256* (2013.01)

(58) Field of Classification Search
CPC ........ A61B 17/17; A61B 17/56; A61B 17/88; A61B 17/68; A61B 17/8061; A61B 17/8872; A61B 17/1757; A61B 17/1671; A61B 17/70; A61B 17/7055; A61B 17/1604; A61B 17/025; A61B 17/1739; A61B 17/84; A61B 17/7074; A61B 17/686; A61B 2017/0256
USPC .............. 606/86 R, 87, 80, 98, 96, 102, 104; 623/17.11–17.16
See application file for complete search history.

(56) References Cited

U.S. PATENT DOCUMENTS

| | | | | |
|---|---|---|---|---|
| 7,648,509 | B2* | 1/2010 | Stark | 606/90 |
| 8,162,981 | B2 | 4/2012 | Vestgaarden | |
| 8,348,950 | B2* | 1/2013 | Assell et al. | 606/79 |
| 8,454,618 | B2 | 6/2013 | Stark | |
| 2006/0054171 | A1* | 3/2006 | Dall | 128/898 |
| 2006/0111782 | A1* | 5/2006 | Petersen | 623/17.11 |
| 2009/0036927 | A1* | 2/2009 | Vestgaarden | 606/247 |
| 2009/0216238 | A1* | 8/2009 | Stark | 606/96 |
| 2009/0259261 | A1* | 10/2009 | Reiley | 606/329 |
| 2014/0336763 | A1* | 11/2014 | Donner et al. | 623/17.11 |

* cited by examiner

*Primary Examiner* — Todd E Manahan
*Assistant Examiner* — Mercela I Shirsat
(74) *Attorney, Agent, or Firm* — Pandiscio & Pandiscio

(57) ABSTRACT

A method for fusing a spinal sacroiliac joint The method includes the steps of locating the sacroiliac joint, retracting the soft tissue to expose the graft site, removing any bone obstructions and preparing a relatively smooth graft site horizontal to the immediate sacroiliac joint, creating a therapeutic cavity by creating a first cavity in the ilium and a second cavity in the sacrum to a predetermined depth that spans the sacroiliac joint, inserting a stabilization implant into the therapeutic cavity, and seating the implant within the therapeutic cavity at a predetermined depth.

14 Claims, 12 Drawing Sheets

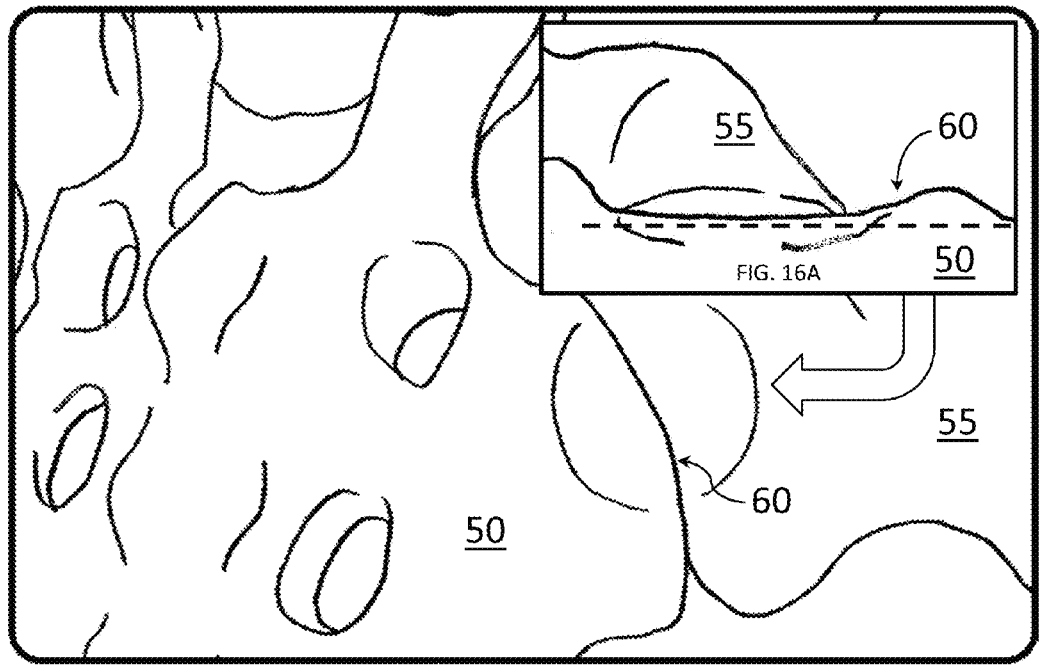
FIG. 16
FIG. 16A
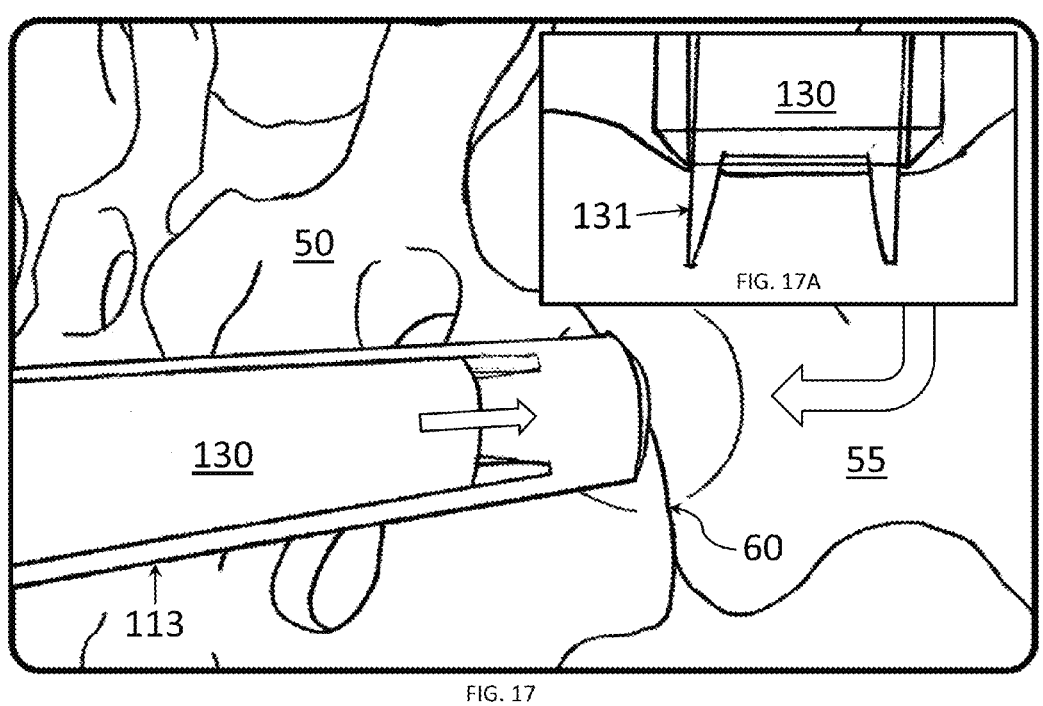
FIG. 17
FIG. 17A

METHOD FOR DEPLOYING A FUSION DEVICE FOR SACROILIAC JOINT FUSION

BACKGROUND OF THE INVENTION

1. Field of the Invention

This invention relates to surgical methods and apparatus in general, and more particularly to surgical methods and apparatus for fusing sacroiliac joints.

2. Description of the Related Art

Lower back pain is a common ailment among the population and results in pain and suffering as well as loss of work time. Effective treatments for lower back pain will alleviate considerable patient suffering and provide economic benefits by reducing employee absenteeism. Until recently, many complaints of lower back pain and leg pain have been attributed to herniated discs or other injuries to the spinal column. However, extensive therapy and treatment has often been unsuccessful in alleviating such pain. Recently, it has been found that some of this lower back and leg pain can be attributed to symptomatic sacroiliac joint dysfunction or instability.

The sacroiliac joint is located at the juncture of the ilium, the upper bone of the pelvis, commonly called the hip bone, and the sacrum at the base of the lumbar spine, where it connects with the L5 vertebra. The function of the sacroiliac joint is the transmission of forces from the spine to the lower extremities and vice-versa. The joint is supported by a range of ligaments, including the sacroiliac ligament at the base of the joint and the anterior sacroiliac ligament at the top of the joint.

The sacroiliac joint has a limited range of motion. Nutation, the relative movement between the sacrum and ilium, is typically one to two degrees. Despite the limited range of motion, a patient's sacroiliac joint can become damaged resulting in hypermobility of the joint. Hypermobility is very difficult to diagnose due to the small range of motion. Therefore, lower back pain or leg pain caused by sacroiliac joint dysfunction, e.g. degenerative sacroiliitis, inflammatory sacroiliitis, iatrogenic instability of the sacroiliac joint, osteitis condensans ilii, or traumatic fracture dislocation of the pelvis, often goes misdiagnosed or undiagnosed.

In patients where sacroiliac joint pain is unresponsive to non-operative treatments, e.g. medication, physical therapy, chiropractic care and steroid injections, surgical stabilization is prescribed. Fusion is a surgical treatment to relieve pain generated from joint dysfunction.

Accordingly, it is a general objective of this invention to provide a method to deliver a device for correcting symptomatic sacroiliac joint dysfunction or instability, for enhancing stability for purposes of immobilizing a joint, and for fusing two opposed bone structures across the joint.

SUMMARY OF THE INVENTION

The long-standing but heretofore unfulfilled need for improved devices and methods for effecting sacroiliac joint fusion is now met by a new, useful, and nonobvious invention.

The present invention includes a surgical kit for use in a method for fusing a sacroiliac joint, preferably including a stabilization implant, a guide pin, a joint locator, dilation tubes, cutting tools such as a reamer or cannulated reamer, a drill bit, a cutter, and a punch, a novel directional cannula, a novel taping cap, a novel drill guide, and a novel implant positioner.

The invention further includes a method for fusing a sacroiliac joint with an implant, preferably comprising the steps of locating the sacroiliac joint, inserting a guide pin or a joint locator into the sacroiliac joint normal to the immediate bone surfaces on either side of the joint, retracting soft tissue via dilation tubes, sliding a cannulated reamer over the guide pin or the joint locator until a distal end of the reamer engages the sacroiliac joint creating a relatively flat graft site, removing the reamer and guide pin or joint locator, inserting a directional cannula into the sacroiliac joint aligning the teeth located on the distal end of the cannula with the plane of the joint, tapping a proximal end of the directional cannula to reversibly secure the alignment teeth into the sacroiliac joint, inserting the drill guide into the directional cannula, inserting a drill bit through the drill guide and drilling a cavity within the sacroiliac joint to a predetermined depth, removing the drill bit from within the drill guide, removing the drill guide from within the directional cannula, inserting the implant through the directional cannula until the distal end of the implant engages the cavity, inserting an implant positioner to seat the implant at a prescribed depth completely within the cavity, proportionately distributed in the sacrum and ilium, removing the implant positioner from within the directional cannula, removing the directional cannula, and removing the dilation tube.

These and other features of the invention will become apparent from the following detailed description of the preferred embodiments of the invention.

The present invention includes a novel apparatus for effecting sacroiliac joint fusion. The novel structure includes a sacroiliac joint stabilization implant for disposition between the opposing articular surfaces of a sacroiliac joint to immobilize the sacroiliac joint and facilitate fusion between the sacrum and ilium.

More particularly, in one form of the present invention, the novel sacroiliac joint stabilization implant includes an elongated body having a distal end, a proximal end and a longitudinal axis extending between the distal end and the proximal end. The elongated body has a cross-sectional profile characterized by a primary axis and a secondary axis, and at least one stabilizer extending radially outwardly from the elongated body in the secondary axis.

The elongated body has a length along the primary axis which is less than the combined width of the sacrum and ilium making up a sacroiliac joint, and at least one stabilizer has a width that is sized to make a press fit into the gap between the sacrum and ilium making up a sacroiliac joint.

A novel method for fusing a sacroiliac joint includes the steps of providing a sacroiliac joint stabilization implant having an elongated body having a distal end, a proximal end and a longitudinal axis extending between the distal end and the proximal end. The method further includes the steps of providing the elongated body with a cross-sectional profile characterized by a primary axis and a secondary axis and providing at least one stabilizer that extends radially outwardly from the elongated body in the secondary axis.

The method steps further include the steps of forming the elongated body so that it has a length along the primary axis which is less than the combined width of the sacrum and the ilium making up a sacroiliac joint and forming the at least one stabilizer so that it has a width sized to make a press fit into the gap between the sacrum and ilium making up a sacroiliac joint.

Further method steps include the steps of deploying the sacroiliac joint stabilization implant in the sacroiliac joint so that the elongated body is simultaneously positioned within the sacrum and ilium of the sacroiliac joint and so that the at least one stabilizer is positioned within the gap between the sacrum and ilium and maintaining the sacroiliac joint stabilization implant in such position while fusion occurs.

Still further steps include deploying the stabilization implant in the joint so that the elongated body is simultaneously positioned within both of the bones of the joint and at least one stabilizer is positioned within the gap between the bones and maintaining the stabilization implant in this position while fusion occurs.

BRIEF DESCRIPTION OF THE DRAWINGS

These and other objects and features of the present invention will be more fully disclosed by the following detailed description of the preferred embodiments of the invention, which is to be considered together with the accompanying drawings wherein like numbers refer to like parts, and further wherein:

FIG. 16 is a perspective view of a relatively flat graft site created horizontal to said sacroiliac joint;

FIG. 16A is a longitudinal sectional view of said graft site of FIG. 16;

FIG. 17 is a perspective view of said directional cannula ensleeved within the lumen of said largest diameter dilation tube;

FIG. 17A is a longitudinal sectional view of the distal end of the said directional cannula positioned in the sacroiliac joint of FIG. 17;

DETAILED DESCRIPTION OF THE PREFERRED EMBODIMENT

Figure 1:
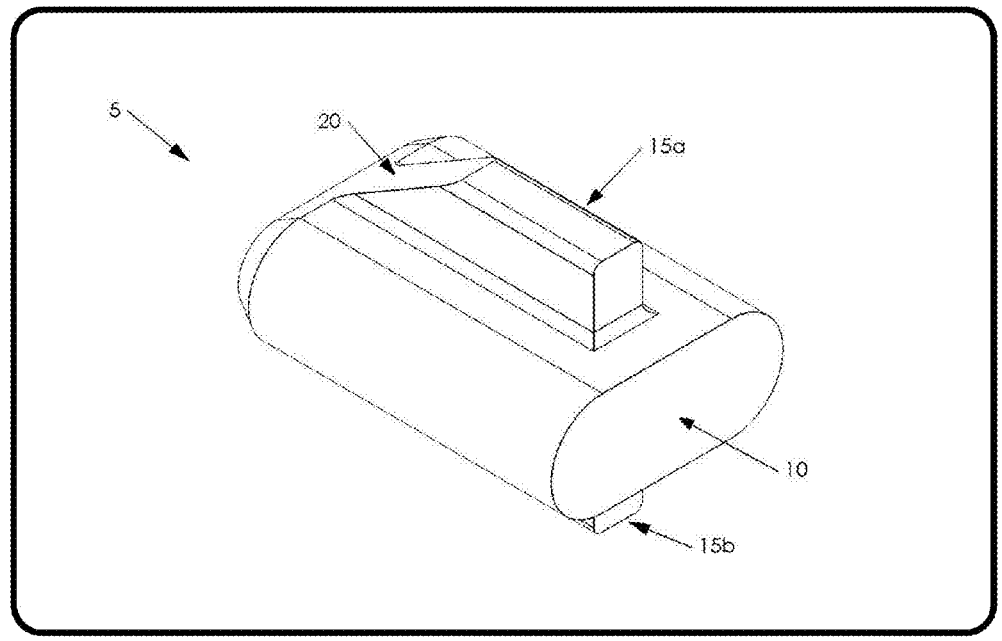
FIG. 1 illustrates a stabilization implant formed in accordance with the present invention.

Referring now to FIG. 1, it will there be seen that the novel sacroiliac stabilization implant, disclosed further in U.S. Pat. No. 8,162,981 to Vestgaarden, entitled "Method and Apparatus for Spinal Facet Fusion," incorporated herein by reference, is denoted as a whole by the reference numeral 5. Stabilization implant 5 generally includes body 10 and at least one stabilizer 15.

Body 10 is an elongated element having structural integrity. Preferably the distal end of body 10 (and the distal end of stabilizer 15 as well) is chamfered as shown at 20 to facilitate insertion of fusion implant 5 into the sacroiliac joint. Preferably, as depicted in FIG. 1, body 10 has a rounded rectangular cross-section, or an ovoid cross-section, a laterally-extended cross-section, or some other non-round cross-section, so as to inhibit rotation of body 10 about a longitudinal center axis.

At least one stabilizer 15 is received in the gap located between the opposing sacroiliac surfaces to prevent rotation of stabilization implant 5 within the sacroiliac joint. In one preferred embodiment of the invention, two stabilizers 15a and 15b are provided, one disposed along the upper surface of body 10 and one disposed along the lower surface of body 10. Stabilizers 15 preferably have a width just slightly larger than the gap between the opposing articular surfaces of a sacroiliac joint so that the stabilizers can make a snug fit therebetween.

Stabilization implant 5 is inserted into a sacroiliac joint using a posterior approach. The posterior approach is familiar to spine surgeons, thereby providing an increased level of comfort for the surgeon.

Figure 2:
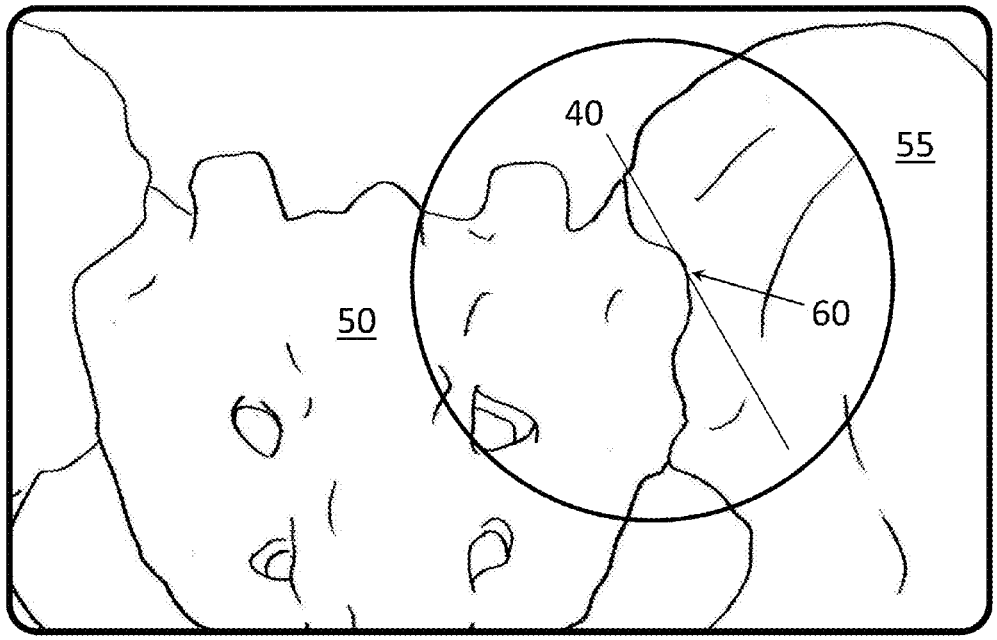
FIG. 2 is a perspective view of a sacroiliac joint.

In use, and referring now at FIG. 2, an instrument is first used to determine plane 40 of sacroiliac joint 60. Identifying the plane of the sacroiliac joint is important, since this is used to identify the proper position for cavity 45 (FIG. 3A) which is to be formed across the sacroiliac joint to receive stabilization implant 5.

At least one of the instruments includes a directional feature which is used to maintain the alignment of the instrumentation with the plane of the sacroiliac joint. A directional cannula may include a flat portion and the remaining instruments may include a flat portion on an opposite portion of the instrument so that the instruments may only be inserted through the cannula at zero degrees (0°), one hundred eighty degrees (180°), or both.

The directional cannula provides the passageway for the placement and insertion of a stabilization device, as well as for performing drilling/cutting or other preparatory work for appropriate stabilization device embodiments.

The directional cannula can have an interior central passage of a circular cross section, oval cross section, rectangular cross section or other desired shape that provides the desired guide channel to deliver a stabilization device into cavity 45.

After the proper position for cavity 45 has been identified, a drill (or reamer, punch, dremel, router, burr, etc.) is used to form cavity 45 in sacroiliac joint 60. Cavity 45 is formed across plane 40 so that substantially one-half of cavity 45 is formed in sacrum 50, and substantially one-half is formed in ilium 55. In the claims that follow, cavity 45 is referred to as the therapeutic cavity. The part of the therapeutic cavity formed in the ilium is referred to as the first cavity and the part of the therapeutic cavity formed in the sacrum is called the second cavity. The therapeutic cavity is defined as including the first and second cavities as well as the sacroiliac joint space. Accordingly, the first cavity is recited as being in open communication with the sacroiliac joint space and the second cavity is recited as being in open communication with the sacroiliac joint space as well. The provision of the therapeutic space enables the insertion of a stabilizer in the therapeutic space while maintaining the iliac and the sacrum in their natural positions, thereby eliminating the prior art method of forcing the sacrum and iliac to move away from one another by employing a wedge-like device that forcibly increases the sacroiliac joint space.

Figure 3A:
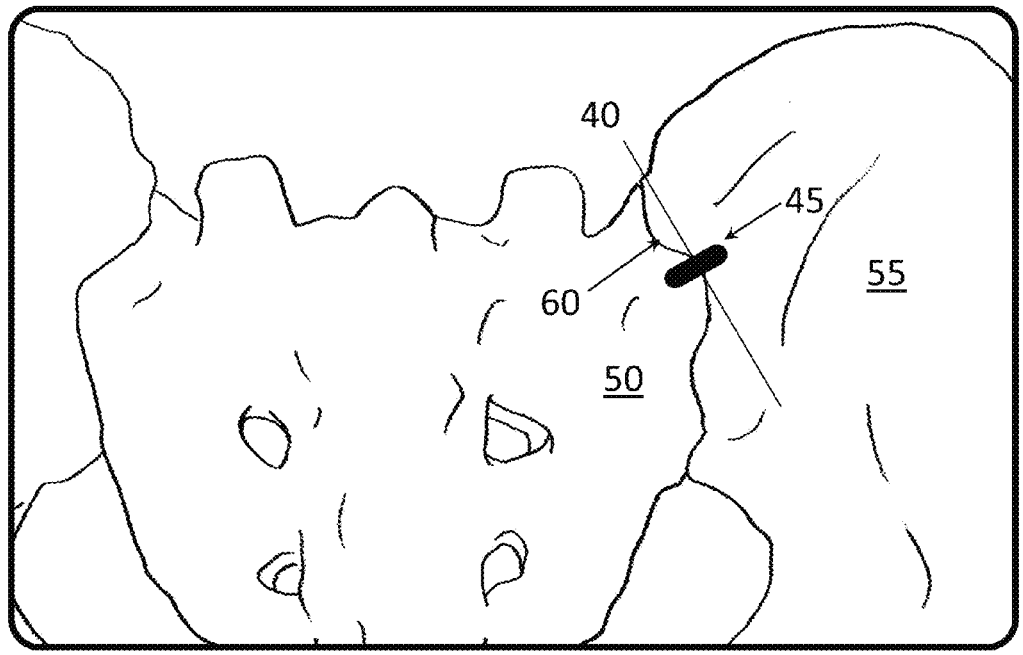
FIG. 3A is a close-up perspective view of said sacroiliac joint and a drilled, bored, punched, or cut cavity.
Figure 3B:
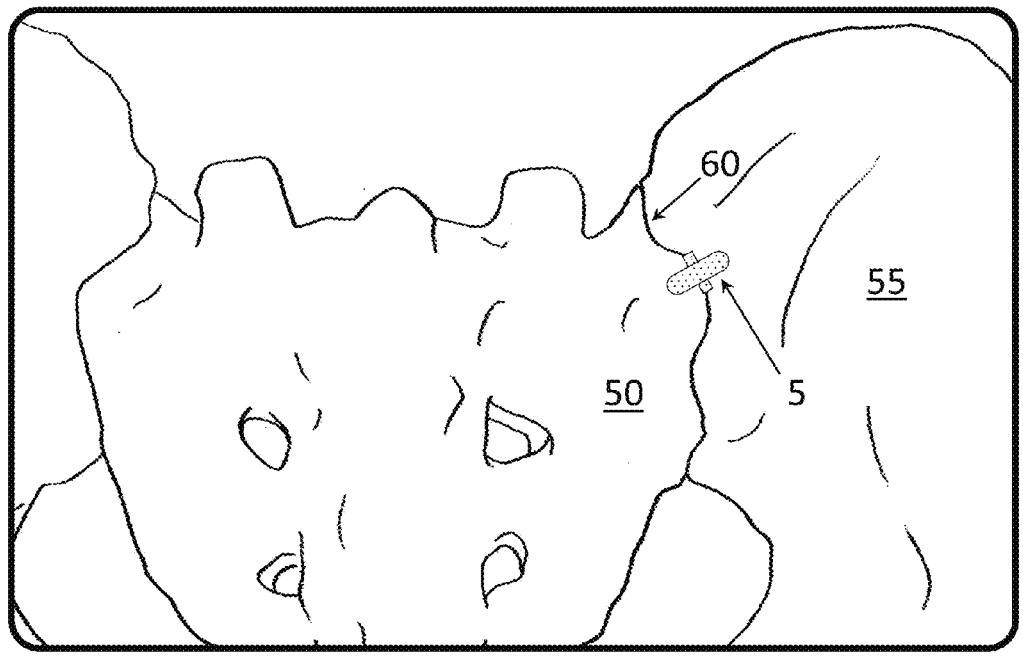
FIG. 3B is a close-up perspective view of said sacroiliac joint and said stabilization implant in the final position in the sacroiliac joint.

After cavity 45 has been formed in (or, perhaps more literally, across) the sacroiliac joint 60, and now referring to FIG. 3B, stabilization implant 5 is inserted into cavity 45. More particularly, stabilization implant 5 is inserted into cavity 45 so that (i) main body 10 spans the gap between opposing sacrum 50 and ilium 55, and (ii) stabilizers 15 extend between the opposing sacrum and ilium surfaces. Preferably, stabilization implant 5 is slightly oversized relative to cavity 45 so as to create a press fit. Stabilization implant 5 provides the stability and strength needed to immobilize the sacroiliac joint 60 while fusion occurs. Due to the positioning of stabilizers 15 between the opposing sacrum and ilium surfaces, and due to the non-circular cross-section of main body 10, stabilization implant 5 is held against rotation within cavity 45, which will in turn holds sacrum 50 and ilium 55 stable relative to one another.

Detailed Surgical Technique

Figure 4:
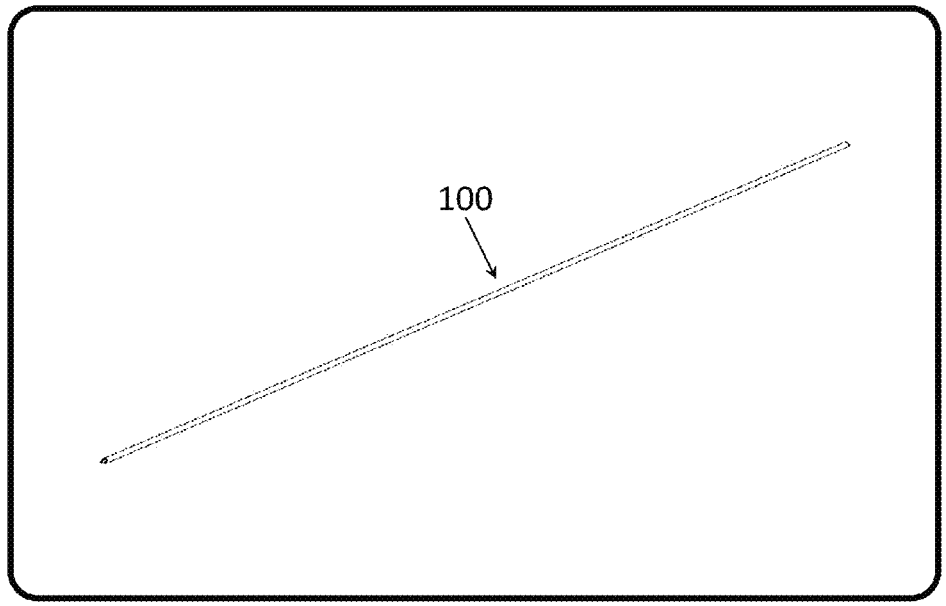
FIG. 4 is a perspective view of a guide pin.
Figure 5:
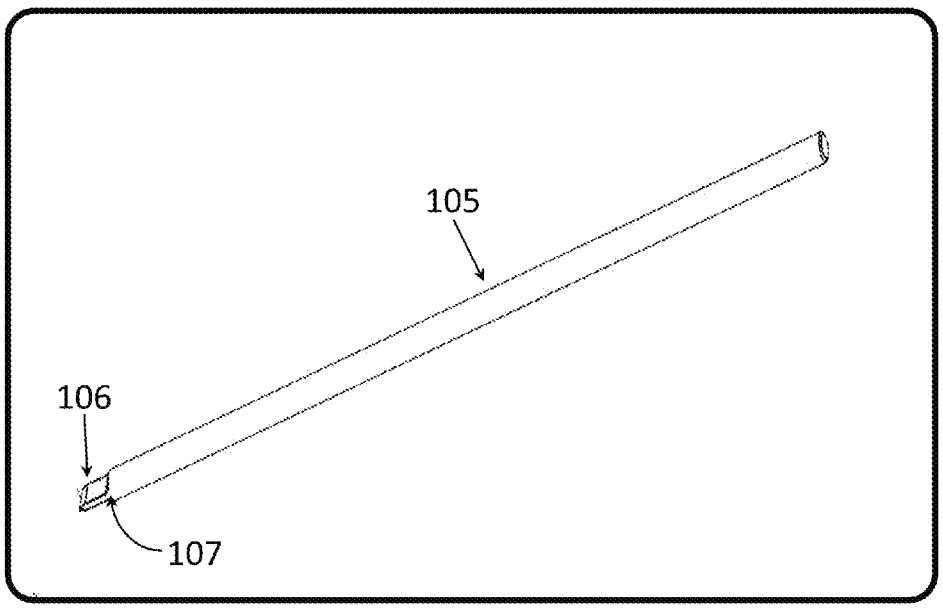
FIG. 5 is a perspective view of a joint locator.
Figure 6:
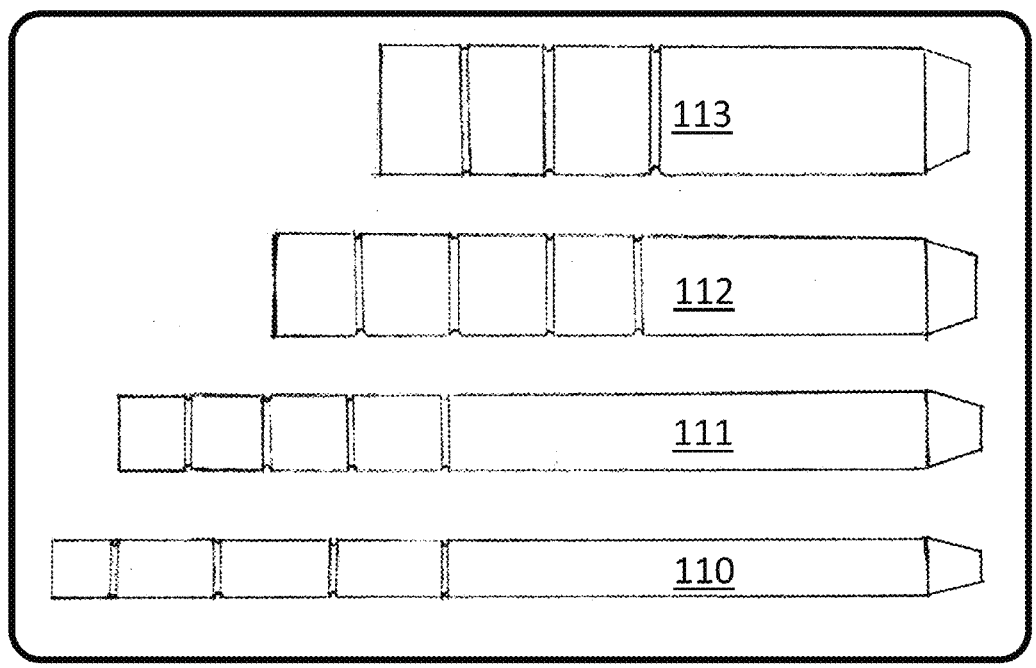
FIG. 6 is a perspective view of four dilation tubes of increasing diameters.
Figure 7:
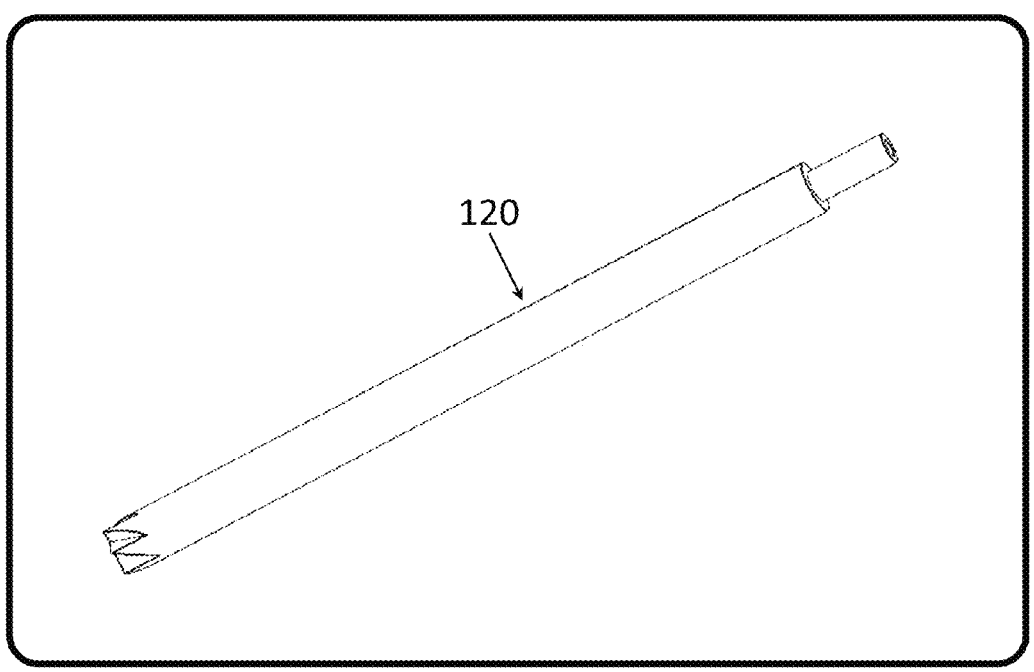
FIG. 7 is a perspective view of a cannulated reamer.
Figure 8:
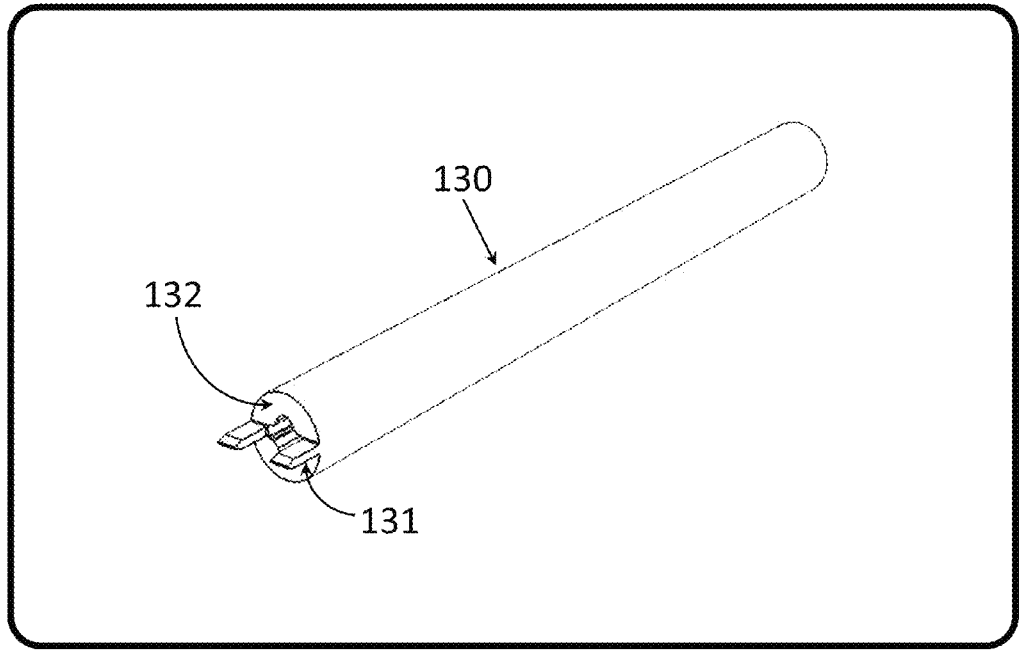
FIG. 8 is a perspective view of a novel directional cannula.
Figure 9:
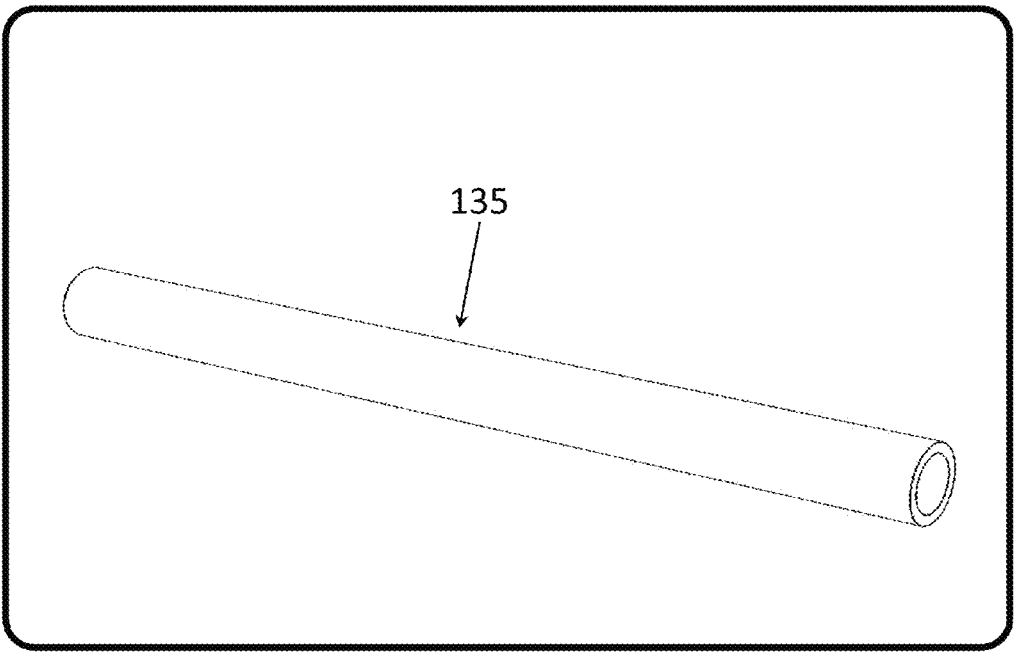
FIG. 9 is a perspective view of a novel tapping cap.
Figure 10:
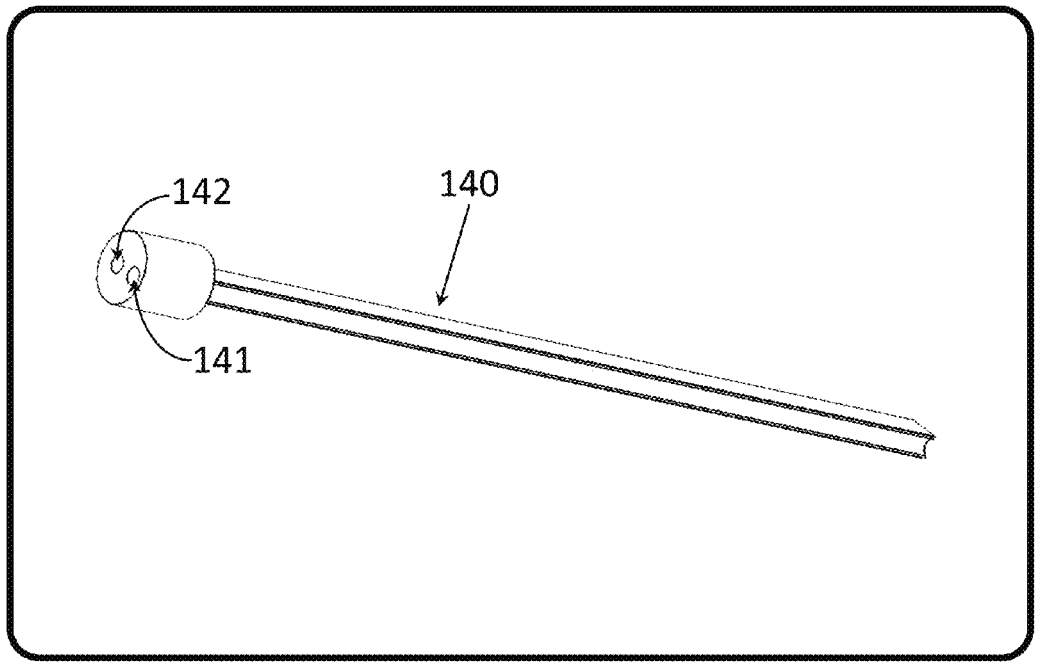
FIG. 10 is a perspective view of a novel drill guide.
Figure 11:
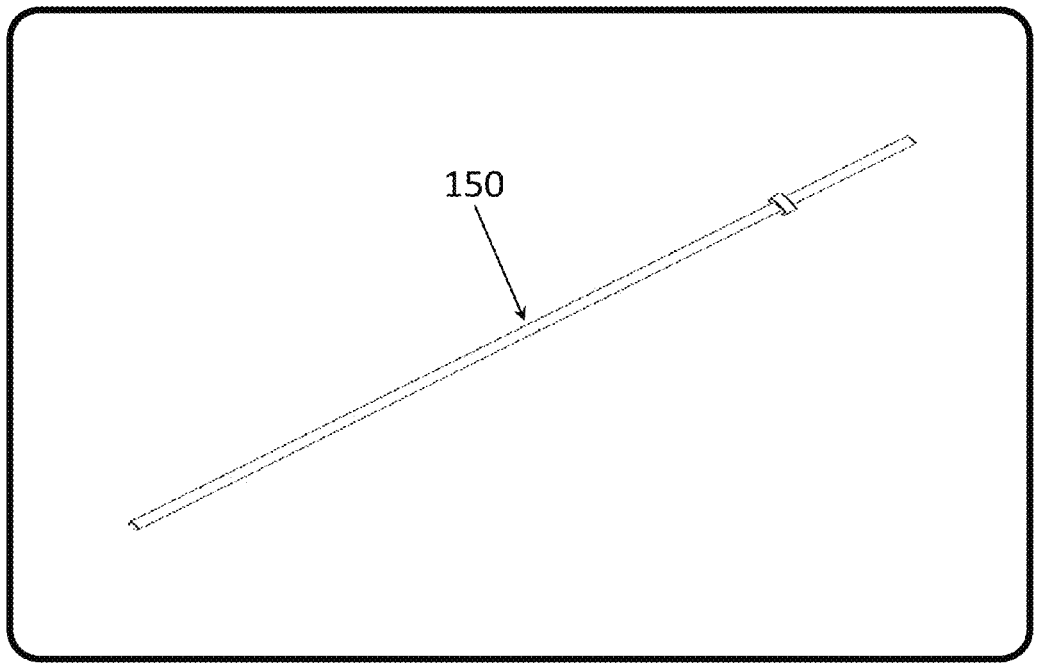
FIG. 11 is a perspective view of a drill bit.
Figure 12:
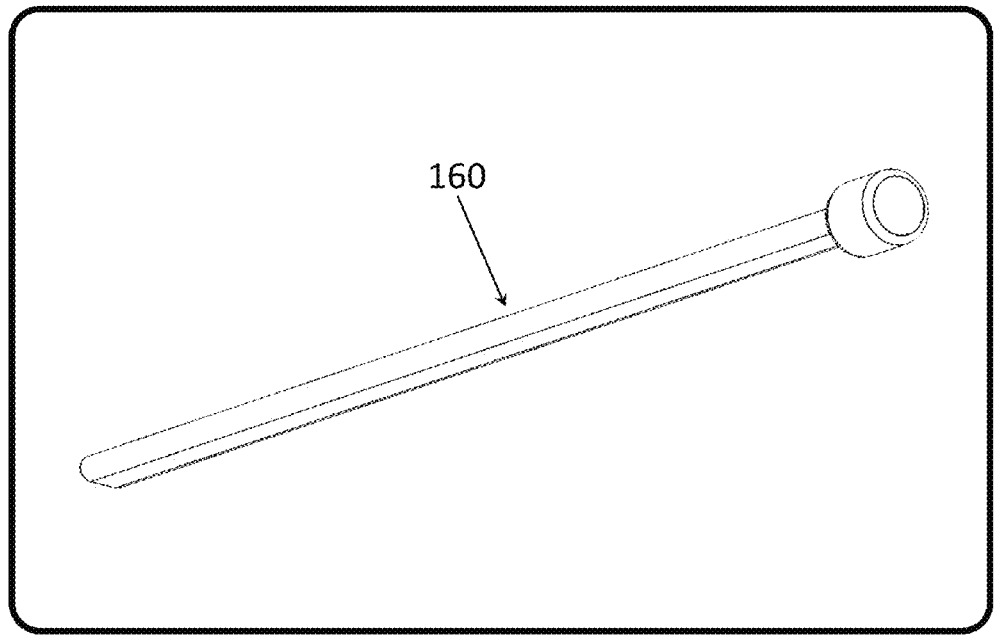
FIG. 12 is a perspective view of a novel implant positioner.

A preferred surgical technique for using stabilization implant 5 employs guide pin 100 (FIG. 4), joint locator 105 (FIG. 5), dilation tubes 110-113 (FIG. 6), cannulated reamer 120 (FIG. 7), directional cannula 130 (FIG. 8), tapping cap 135 (FIG. 9), drill guide 140 (FIG. 10), drill bit 150 (FIG. 11), and implant positioner 160 (FIG. 12)

First, the sacroiliac joint is localized indirectly by fluoroscopy, or directly by visualization during an open procedure. A path through soft tissue to the sacroiliac joint is then created via surgeon's preference, such as open, minimally-invasive, percutaneous, or arthroscopic.

A set of dilation tubes 110-113 (FIG. 13) having increasing diameters is then inserted into the soft tissue opening in sequence of increasing diameters to sufficiently retract the soft tissue exposing a graft site.

Figure 14:
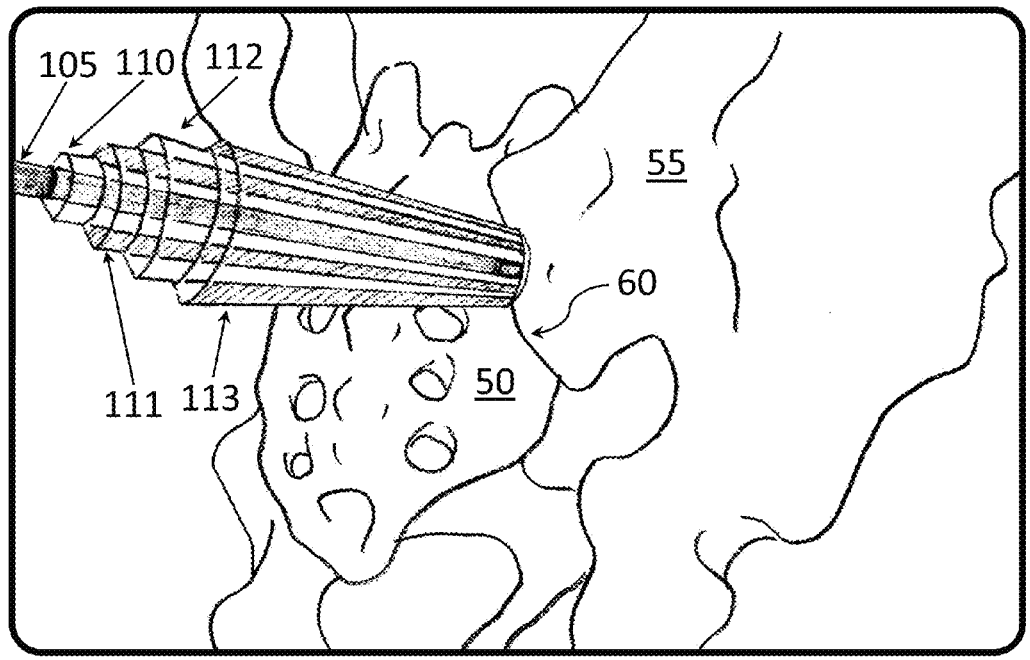
FIG. 14 is a perspective view of a said dilation tubes with said joint locator ensleeved within a lumen of the smallest diameter dilation tube.

Next, joint locator 105 (FIG. 14) is slid into a lumen of dilation tube 110 until blade 106 engages sacroiliac joint 60 and is aligned with joint plane 40. Then joint locator 105 is lightly tapped so as to insert joint locator blade 106 into sacroiliac joint 60 until positive stop 107 is engaged.

Next, internal dilation tubes 110-112 are removed from within the lumen of dilation tube 113.

Figure 15:
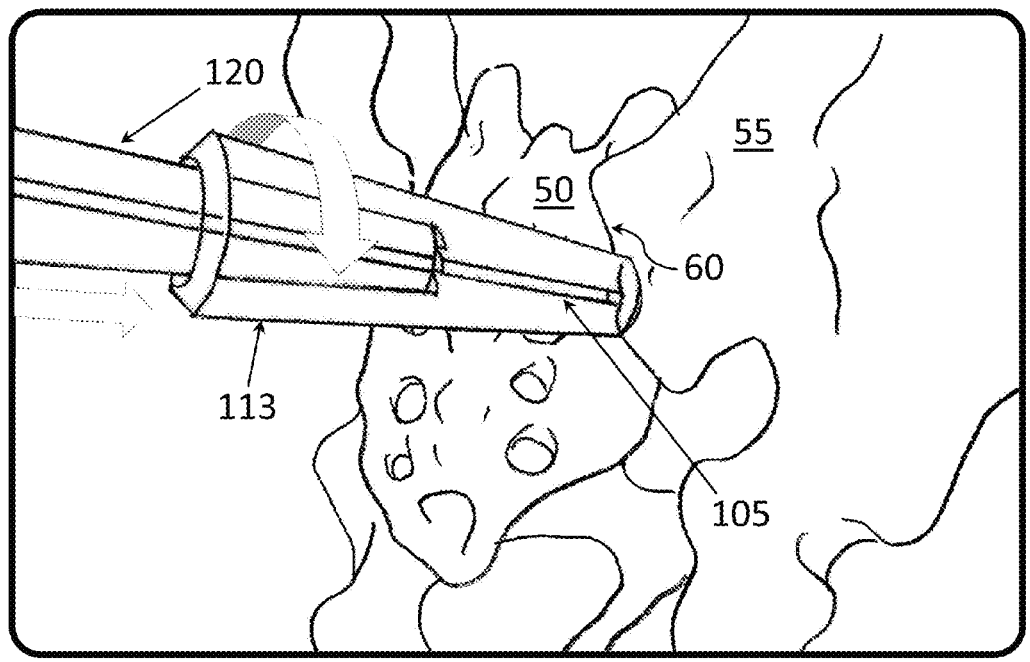
FIG. 15 is a perspective view of said cannulated reamer ensleeved within the lumen of the largest diameter dilation tube, sliding over said joint locator.

Cannulated reamer 120 is then slid over joint locator 105 to remove any bone obstructing the joint and to prepare the graft surface for receiving directional cannula 130 and stabilization implant 5 (FIG. 15). The distal end of reamer 120 is advanced until it sufficiently engages sacroiliac joint 60, thereby preparing a relatively flat graft surface perpendicular to sacroiliac joint 60 (FIGS. 16 and 16A). The position of reamer 120 and joint locator 105 is verified by viewing the coronal and sagittal planes.

Reamer 120 and joint locator 105 are then removed from within the lumen of dilation tube 113.

Next, directional cannula 130 is inserted into the lumen of dilation tube 113 until a distal end of cannula 130 engages sacroiliac joint 60 (FIG. 17). Directional cannula teeth 131 are then aligned with plane 40 of sacroiliac joint 60. Once teeth 131 of cannula 130 are aligned with plane 40, directional cannula 130 is lightly tapped to insert cannula teeth 131 into sacroiliac joint 60 until positive stop 132 engages sacroiliac joint 60 (FIG. 17A).

Figure 18:
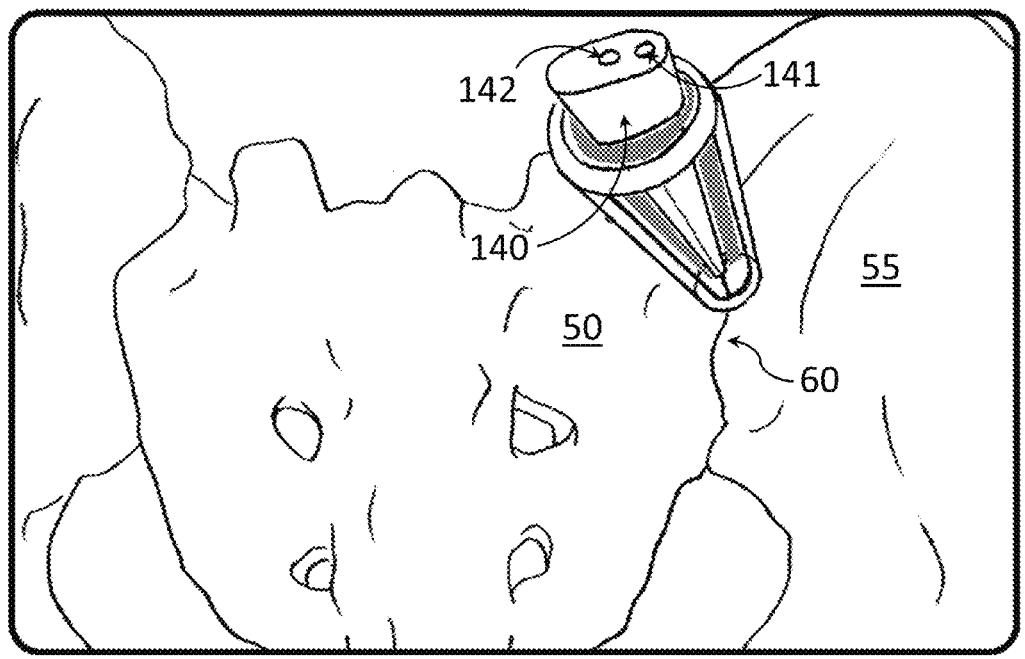
FIG. 18 is a perspective view of said drill guide ensleeved in the lumen of said directional cannula with a non-centered guide hole positioned over an ilium bone.

Drill guide 140 is then inserted into a lumen of directional cannula 130 with non-centered guide hole 141 positioned over iliac bone 55 (FIG. 18). Drill guide 140 is advanced within the lumen of directional cannula 130 until drill guide 140 reaches a mechanical stop on directional cannula 130. Then, with drill guide 140 in place, irrigation fluid (e.g., a few drops of saline) is placed into the drill guide hole 141 positioned over iliac bone 55. Next, drill bit 150 is inserted into guide hole 141 and used to drill a cavity in iliac bone 55. Drilling continues until drill bit 150 reaches a mechanical stop on drill guide 140. Then drill bit 150 is removed from the lumen of guide hole 141. Next, with drill guide 140 remaining in position, irrigation fluid (e.g., a few drops of saline) is placed into central guide hole 142 of drill guide 140. Drill bit 150 is then inserted in a lumen of guide hole 142 and used to drill a cavity in sacroiliac joint 60, between sacrum 50 and ilium 55. Next, drill bit 150 is removed from the lumen of guide hole 142. Drill guide 140 is then removed from the lumen of directional cannula 130.

Figure 19:
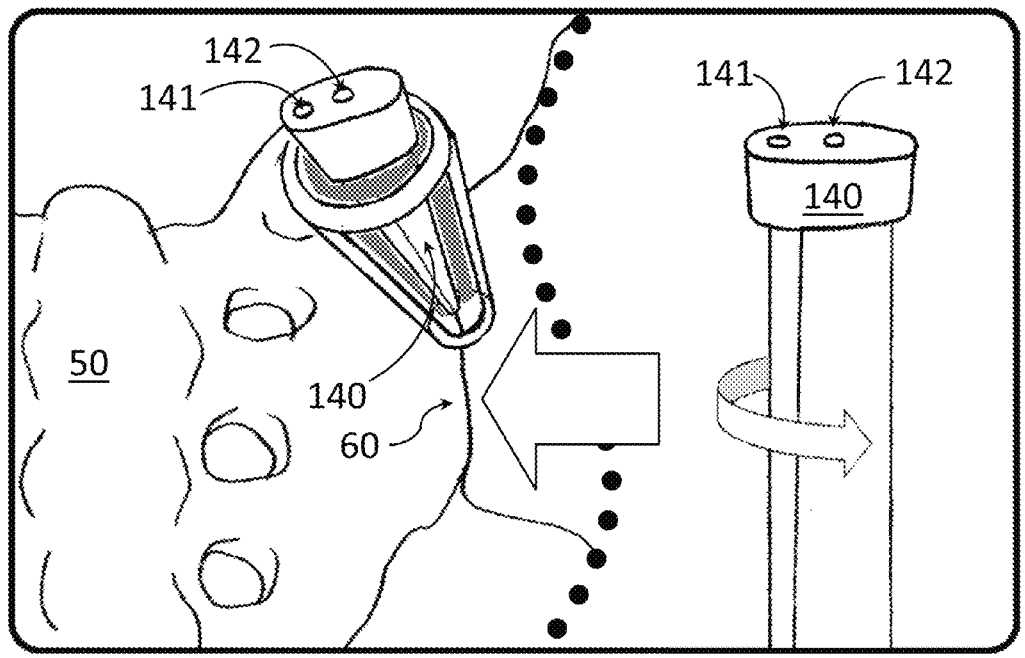
FIG. 19 is a perspective view of said drill guide rotated 180 degrees and subsequently ensleeved in the lumen of said directional cannula with said non-centered guide hole now positioned over a sacrum bone.

Drill guide 140 is rotated 180 degrees, and is reinserted into the lumen of directional cannula 130 in order to drill sacrum 50 (FIG. 19). With drill guide 140 in place, irrigation fluid (e.g., a few drops of saline) is placed into drill guide hole 141, now positioned over sacrum 50. Next, drill bit 150 is inserted into the lumen of guide hole 141 and used to drill a cavity in sacrum bone 50. Drilling continues until drill bit 150 reaches a mechanical stop on drill guide 140. Then drill bit 150 is removed from the lumen of guide hole 141. Next, with drill guide 140 remaining in position, irrigation fluid (e.g., a few drops of saline) is placed into central guide hole 142 of drill guide 140. Next, drill bit 150 is inserted into guide hole 142 and used to drill a cavity in sacroiliac joint 60, between sacrum 50 and ilium 55. Next, drill bit 150 is removed from guide hole 142 and drill guide 140 is removed from the lumen of directional cannula 130.

Figure 20:
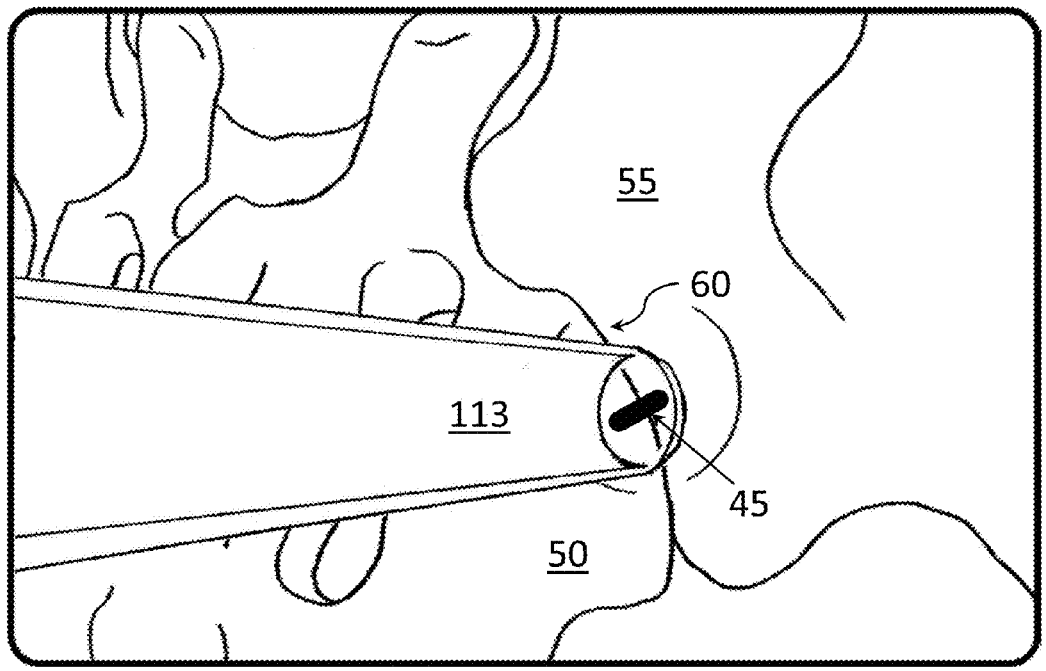
FIG. 20 is a perspective view of said sacrum and ilium bones and a drilled, bored, punched, or cut cavity formed in said sacroiliac joint.

This procedure creates cavity 45 (FIG. 20) that is sufficiently deep and that is proportionately distributed in sacrum 50 and ilium 55 to receive stabilization implant 5.

Figure 21:
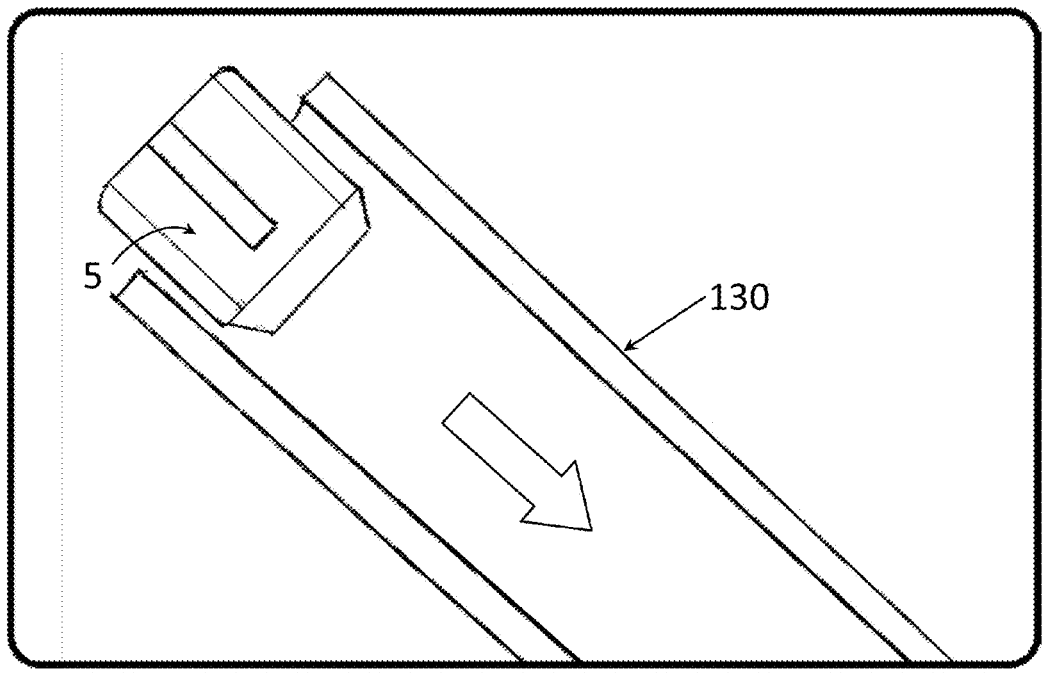
FIG. 21 is an exploded perspective view of said stabilization implant being loaded into said directional cannula.
Figure 22:
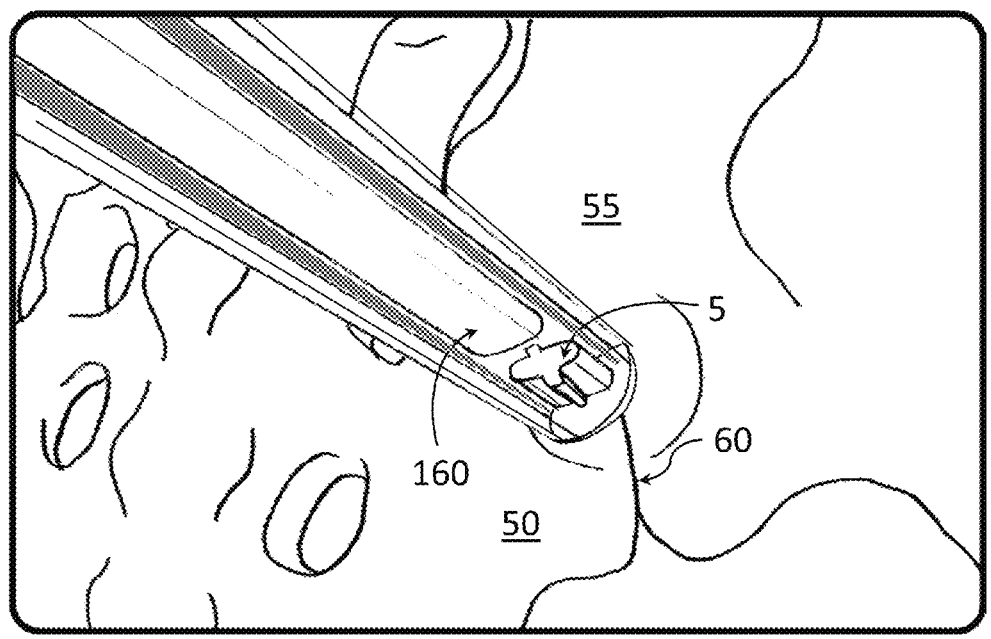
FIG. 22 is a perspective view of said implant and said implant positioner ensleeved in the lumen of the directional cannula prior to final position.
Figure 23:
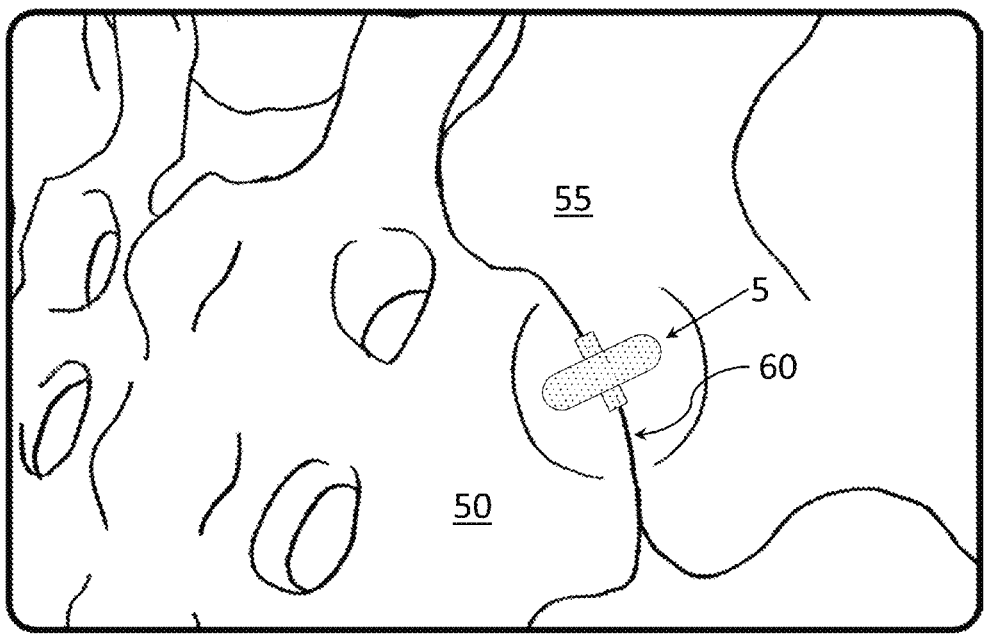
FIG. 23 is a perspective view of said stabilization implant in the final position in said sacroiliac joint.

Stabilization implant 5 is then inserted, distal end first, into the lumen of directional cannula 130 (FIG. 21). Next, implant positioner 160 is inserted into the lumen of directional cannula 130 and advanced until resistance is felt, indicating that the distal end of implant 5 has engaged cavity 45 (FIG. 22). Next, implant positioner 160 is lightly tapped to drive implant 5 into cavity 45 created laterally across sacroiliac joint 60 (FIG. 23). Stabilization implant 5 is preferably countersunk 1-2 mm into sacroiliac joint 60.

Finally, implant positioner 160 and directional cannula 130 are removed from the lumen of dilation tube 113. Dilation tube 113 is then removed from the soft tissue and the incision is closed.

The foregoing steps are repeated for additional locations in the current sacroiliac joint 60 and in contralateral sacroiliac joint 60.

Alternative Surgical Technique

First, sacroiliac joint 60 is localized indirectly by fluoroscopy, or directly by visualization during an open procedure. Guide pin 100 is inserted into sacroiliac joint 60, normal to immediate opposing joint surfaces when sacroiliac joint 60 is exposed, or drilled into joint 60 through the iliac crest when sacroiliac joint 60 is obstructed. The position of guide pin 100 is determined by viewing the coronal and sagittal planes.

Guide pin 100 is then lightly tapped to insert guide pin 100 approximately 15-20 mm into sacroiliac joint 60, along joint plane 40 (FIG. 3A)

Figure 13:
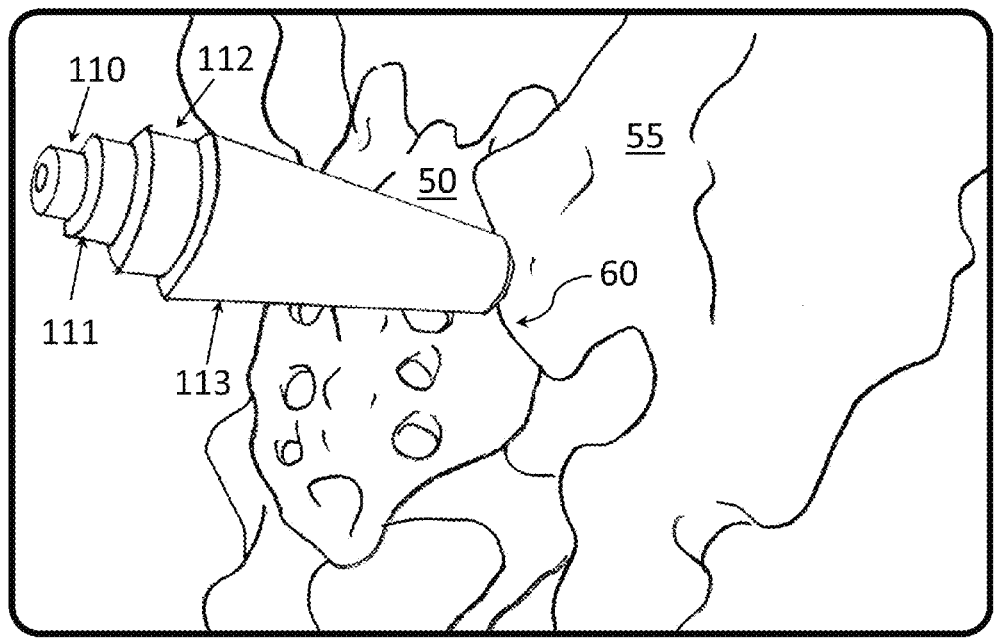
FIG. 13 is a perspective view of said dilation tubes positioned over said sacroiliac joint.

Next, a set of dilation tubes 110-113 (FIG. 6) having increasing diameters is slid over guide pin 100 into the soft tissue in sequence of increasing diameters to sufficiently retract soft tissue exposing a graft site (FIG. 13). Once a sufficient surgical area is exposed, internal dilation tubes 110-112 are removed from within the lumen of dilation tube 113.

Next, referring to FIG. 15, cannulated reamer 120 is slid over guide pin 100 within the lumen of dilation tube 113 to remove any bone obstructing sacroiliac joint 60 and to prepare the graft surface for receiving directional cannula 130 and fusion implant 5. The distal end of reamer 120 is advanced until it sufficiently engages sacroiliac joint 60, thereby preparing a relatively flat graft surface perpendicular to sacroiliac joint 60 (FIGS. 16A and 16B). The position of reamer 120 is verified by viewing the coronal and sagittal planes.

Next, reamer 120 and guide pin 100 are removed from within the lumen of dilation tube 113.

The previously disclosed steps of removing reamer 120 and joint locator 105 from within the lumen of dilation tube 113 through removing implant positioner 160 and directional cannula 130 from the lumen of dilation tube 113, removing dilation tube 113 from the soft tissue, and closing the incision are followed to complete the procedure.

Numerous advantages are achieved by the present invention. For example, the present invention provides a fast, simple, minimally-invasive and easily reproduced approach for effecting sacroiliac joint fusion.

While stabilization implant 5 has been disclosed above in the context of fusing a sacroiliac joint, it should also be appreciated that stabilization implant 5 may be used to stabilize and fuse any joint having anatomy similar to the sacroiliac joint, i.e., a pair of opposing bony surfaces defining a gap therebetween, with the stabilizer of the stabilization implant being sized to be positioned within the gap. By way of example but not limitation, the stabilization implant may be used in small joints such as the fingers, toes, etc.

It should be understood that many additional changes in the details, materials, steps and arrangements of parts, which have been herein described and illustrated in order to explain the nature of the present invention may be made by those skilled in the art while still remaining within the principles and scope of the invention.

It will be seen that the advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

What is claimed is:

1. A method for fusing a sacroiliac joint, comprising the steps of:
creating a therapeutic cavity by creating a first cavity in an iliac bone and a second cavity in a sacrum, said first cavity being in open communication with said sacroiliac joint, said second cavity being in open communication with said sacroiliac joint, said therapeutic cavity formed by said first cavity, said second cavity, and said sacroiliac joint,
wherein a resulting cavity is formed between said first and second cavities in said sacroiliac joint by the empty space of said sacroiliac joint,
said therapeutic cavity formed by
creating one of said first cavity and said second cavity, and
creating another of said first cavity and said second cavity after creation of said one of said first cavity and said second cavity, and
wherein said resulting cavity is formed in said sacroiliac joint by empty space in said sacroiliac joint;
maintaining said iliac bone and said sacrum in their respective positions while creating said first and second cavities; and
filling said cavity with a bone void filler;
wherein creating the therapeutic cavity comprises:
exposing the sacroiliac joint with a set of dilation tubes having increasing diameters;
sliding a joint locator within the lumen of the smallest diameter dilation tube until a distal end of said joint locator engages the sacroiliac joint so that a joint locator blade distally located on said joint locator aligns in the sacroiliac joint;
tapping a proximal end of said joint locator to reversibly secure said joint locator blade into the sacroiliac joint;
removing the interior dilation tubes;
abrading sacroiliac joint surfaces using said joint locator blade;
sliding a cannulated reamer over said joint locator until a distal end of said reamer engages the sacroiliac joint, creating a relatively flat horizontal graft site;
removing said reamer and said joint locator from within a lumen of the dilation tube;
inserting a directional cannula into the dilation tube until a distal end of said directional cannula engages the sacroiliac joint so that alignment teeth distally located on said directional cannula align in the sacroiliac joint;
tapping a proximal end of said directional cannula to reversibly secure said alignment teeth into the sacroiliac joint;
aligning a drill guide over said directional cannula so that a non-centered guide hole is positioned over the iliac bone;
inserting said aligned drill guide into a lumen of said directional cannula until a positive stop on said directional cannula is engaged;
inserting a drill bit through said non-centered drill guide hole and drilling a cavity within the iliac bone to a predetermined depth;
removing said drill bit from a lumen of said drill guide;
removing said drill guide from said lumen of said directional cannula;
rotating said drill guide one hundred eighty degrees (180°), aligning said drill guide over said directional cannula so that said non-centered guide hole is positioned over the sacrum;
inserting said aligned drill guide into said lumen of said directional cannula until said positive stop on said directional cannula is engaged;
inserting said drill bit through said non-centered drill guide hole, now positioned over the sacrum, and drilling a cavity within the sacrum to a predetermined depth;
removing said drill bit from the lumen of said drill guide;

inserting said drill bit through a centered drill guide hole and drilling a cavity within the sacroiliac joint to a predetermined depth;

removing said drill bit from said lumen of said drill guide, and removing said drill guide from said lumen of said directional cannula;

wherein filling said cavity with the bone void filler comprises:

inserting a stabilization implant through said lumen of said directional cannula;

inserting an implant positioner into said lumen of said directional cannula until said implant positioner engages said implant, and a distal end of said implant engages said therapeutic cavity;

tapping a proximal end of said implant positioner until a positive stop on said directional cannula is engaged to properly seat said implant into said therapeutic cavity, at a prescribed depth completely within said therapeutic cavity, proportionately distributed laterally across the sacroiliac joint engaging the sacrum and the ilium;

removing said implant positioner from said lumen of said directional cannula;

removing said directional cannula from said sacroiliac joint; and removing the dilation tube from said soft tissue.

2. A method for fusing a sacroiliac joint according to claim 1 wherein said step of drilling the cavity within the iliac bone comprises punching said cavity within the iliac bone and said step of drilling the cavity within the sacrum comprises punching said cavity within the sacrum.

3. A method for fusing a sacroiliac joint according to claim 1 wherein the stabilization device is associated with a bone growth promoter.

4. A method for fusing a sacroiliac joint according to claim 1, wherein creating the therapeutic cavity further comprises:
localizing the sacroiliac joint.

5. A method for fusing a sacroiliac joint according to claim 1, wherein exposing the sacroiliac joint with the set of dilation tubes having increasing diameters comprises:
localizing the sacroiliac joint;
inserting a guide pin into the sacroiliac joint;
sliding the set of dilation tubes having increasing diameters over said guide pin to sufficiently retract soft tissue exposing a graft site; and
removing said guide pin from within the set of dilation tubes.

6. A method for fusing a sacroiliac joint comprising the steps of:

creating a therapeutic cavity by creating a first cavity in an iliac bone and a second cavity in a sacrum, said first cavity being in open communication with said sacroiliac joint, said second cavity being in open communication with said sacroiliac joint, said therapeutic cavity formed by said first cavity, said second cavity, and said sacroiliac joint, wherein a resulting cavity is formed between said first and second cavities in said sacroiliac joint by the empty space of said sacroiliac joint, said therapeutic cavity formed by
creating one of said first cavity and said second cavity, and
creating another of said first cavity and said second cavity after creation of said one of said first cavity and said second cavity, wherein said resulting cavity is formed in said sacroiliac joint by empty space in said sacroiliac joint;

maintaining said iliac bone and said sacrum in their respective positions while creating said first and second cavities; and filling said cavity with a bone void filler;

wherein creating the therapeutic cavity comprises:
localizing the sacroiliac joint;
inserting a joint locator into the sacroiliac joint until a distal end of said joint locator engages the sacroiliac joint so that a joint locator blade distally located on said joint locator aligns in the sacroiliac joint;

tapping a proximal end of said joint locator to reversibly secure said joint locator blade into the sacroiliac joint;

abrading sacroiliac joint surfaces using said joint locator blade;

sliding a directional cannula over said joint locator until a distal end of said directional cannula engages the sacroiliac joint so that alignment teeth distally located on said directional cannula align in the sacroiliac joint;

sliding a tapping cap over said joint locator until a distal end of said tapping cap engages a proximal end of said directional cannula;

tapping said proximal end of said tapping cap to reversibly secure said alignment teeth of said directional cannula into the sacroiliac joint;

removing said tapping cap;

removing said joint locator from within a lumen of said directional cannula;

aligning a drill guide over said directional cannula so that a non-centered guide hole is positioned over the iliac bone;

inserting said aligned drill guide into a lumen of said directional cannula until a positive stop on said directional cannula is engaged;

inserting a drill bit through said non-centered drill guide hole and drilling a cavity within the iliac bone to a predetermined depth;

removing said drill bit from a lumen of said drill guide;

removing said drill guide from said lumen of said directional cannula;

rotating said drill guide one hundred eighty degrees (180°), aligning said drill guide over said directional cannula so that said non-centered guide hole is positioned over the sacrum;

inserting said aligned drill guide into said lumen of said directional cannula until said positive stop on said directional cannula is engaged;

inserting said drill bit through said non-centered drill guide hole, now positioned over the sacrum, and drilling a cavity within the sacrum to a predetermined depth;

removing said drill bit from said lumen of said drill guide;

inserting said drill bit through a centered drill guide hole and drilling a cavity within the sacroiliac joint to a predetermined depth;

removing said drill bit from said lumen of said drill guide, and removing said drill guide from said lumen of said directional cannula;

wherein filling said cavity with the bone void filler comprises:

inserting a stabilization implant through said lumen of said directional cannula;

inserting an implant positioner into said lumen of said directional cannula until said implant positioner engages said implant, and a distal end of said implant engages said therapeutic cavity;

tapping a proximal end of said implant positioner until a positive stop on said directional cannula is engaged to properly seat said implant into said therapeutic cavity, at a prescribed depth completely within said therapeutic cavity, proportionately distributed laterally across the sacroiliac joint engaging the sacrum and the ilium;

removing said implant positioner from said lumen of said directional cannula;

removing said directional cannula from said sacroiliac joint and said soft tissue.

7. A method for fusing a sacroiliac joint, comprising the steps of:

creating a therapeutic cavity by creating a first cavity in a preselected iliac bone and a second cavity in a sacrum, said therapeutic cavity spanning said sacroiliac joint, wherein a resulting cavity is formed between said first and second cavities in said sacroiliac joint by the empty space of said sacroiliac joint, said therapeutic cavity formed by creating one of said first cavity and said second cavity, and creating another of said first cavity and said second cavity after creation of said one of said first cavity and said second cavity, wherein said resulting cavity is formed in said sacroiliac joint by empty space in said sacroiliac joint;

filling said therapeutic cavity with a bone void filler;

wherein creating the therapeutic cavity comprises:

providing a set of dilation tubes having at least a smallest diameter dilation tube, a largest diameter dilation tube and at least one intermediate diameter dilation tube, said at least one intermediate diameter dilation tube having a diameter greater than the diameter of said smallest diameter dilation tube and less than the diameter of said largest diameter dilation tube;

retracting soft tissue with said smallest diameter dilation tube to partially expose a graft site;

increasing the exposure of said graft site by sliding said at least one intermediate diameter dilation tube over said smallest diameter dilation tube; and fully exposing said graft site by sliding said largest diameter dilation tube over said smallest diameter dilation tube;

sliding a joint locator into a lumen of the smallest diameter dilation tube until a distal end of said joint locator engages the sacroiliac joint;

providing a joint locator blade at the distal end of said joint locator;

aligning said joint locator blade in the sacroiliac joint;

tapping a proximal end of said joint locator to reversibly secure said joint locator blade into the sacroiliac joint;

removing the smallest diameter dilation tube and the at least one intermediate diameter dilation tube from a lumen of said largest diameter dilation tube;

abrading sacroiliac joint surfaces using said joint locator blade;

creating a relatively flat horizontal graft site by sliding a cannulated reamer over said joint locator until a distal end of said reamer engages the sacroiliac joint;

removing said reamer and said joint locator from within the lumen of the largest diameter dilation tube;

inserting a directional cannula having a lumen into said lumen of said largest diameter dilation tube until a distal end of said directional cannula engages the sacroiliac joint;

providing alignment teeth on a distal end of said directional cannula;

aligning said alignment teeth in the sacroiliac joint; and tapping a proximal end of said directional cannula to reversibly secure said alignment teeth into the sacroiliac joint.

8. The method of claim 7 wherein creating the therapeutic cavity further comprises:

aligning a drill guide having a lumen over said directional cannula so that a non-centered guide hole defined by said drill guide lumen is positioned over the iliac bone;

inserting said aligned drill guide into said lumen of said directional cannula until a positive stop on said directional cannula is engaged;

inserting a drill bit through said non-centered drill guide hole and drilling an iliac bone cavity within the iliac bone to a predetermined depth;

removing said drill bit from said lumen of said drill guide; and removing said drill guide from said lumen of said directional cannula.

9. The method of claim 8 wherein creating the therapeutic cavity further comprises:

rotating said drill guide one hundred eighty degrees) (180°) to align said drill guide over said directional cannula so that said non-centered guide hole is positioned over the sacrum;

inserting said aligned drill guide into said lumen of said directional cannula until said drill guide engages said positive stop on said directional cannula;

inserting said drill bit, positioned over the sacrum, through said non-centered drill guide hole and drilling a sacrum cavity within the sacrum to a predetermined depth;

removing said drill bit from the lumen of said drill guide;

inserting said drill bit through a centered drill guide hole and drilling a sacroiliac joint cavity within the sacroiliac joint to a predetermined depth;

removing said drill bit from said lumen of said drill guide, and removing said drill guide from said lumen of said directional cannula;

wherein filling said therapeutic cavity with the bone void filler comprises:

inserting a stabilization implant through said lumen of said directional cannula;

inserting an implant positioner into said lumen of said directional cannula until said implant positioner engages said implant, and a distal end of said implant engages said sacroiliac joint cavity;

tapping a proximal end of said implant positioner until a positive stop on said directional cannula is engaged to properly seat said implant into said sacroiliac joint cavity, at a predetermined depth completely within said sacroiliac joint cavity, proportionately distributed laterally across the sacroiliac joint engaging the sacrum and the ilium;

removing said implant positioner from said lumen of said directional cannula;

removing said directional cannula from said sacroiliac joint; and removing said largest diameter dilation tube from said soft tissue.

10. A method for fusing a sacroiliac joint according to claim 7 wherein exposing the graft site further comprises:
  localizing the sacroiliac joint;
  inserting a guide pin into the sacroiliac joint;
  sliding said smallest diameter dilation tube over said guide pin to begin exposing the graft site by retracting soft tissue;
  sliding said largest diameter dilation tube over said smallest diameter dilation tube to fully expose said graft site by further retracting said soft tissue.

11. The method of claim 10 wherein exposing the graft site further comprises
  sliding said at least one intermediate diameter dilation tube over said smallest diameter dilation tube.

12. The method of claim 11, further comprising:
  removing said guide pin, said smallest diameter dilation tube, and said at least one intermediate diameter dilation tube from the lumen of said largest dilation tube.

13. A method for fusing a sacroiliac joint, comprising the steps of:
  providing a joint locator having a blade at a distal end of said joint locator;
  aligning said joint locator blade in the sacroiliac joint;
  inserting said joint locator into the sacroiliac joint until said distal end of said joint locator engages the sacroiliac joint;
  aligning said joint locator blade in the sacroiliac joint;
  tapping a proximal end of said joint locator to reversibly secure said joint locator blade into the sacroiliac joint;
  abrading sacroiliac joint surfaces using said joint locator blade;
  providing a directional cannula;
  providing alignment teeth at a distal end of said directional cannula;
  sliding the directional cannula over said joint locator until said distal end of said directional cannula engages the sacroiliac joint;
  aligning said alignment teeth in the sacroiliac joint;
  sliding a tapping cap over said joint locator until a distal end of said tapping cap engages a proximal end of said directional cannula;
  tapping said proximal end of said tapping cap to reversibly secure said alignment teeth of said directional cannula into the sacroiliac joint;
  removing said tapping cap;
  removing said joint locator from within a lumen of said directional cannula;
  aligning a drill guide over said directional cannula so that a non-centered drill guide hole is positioned over the iliac bone, said drill guide having a lumen that defines said drill guide hole;
  inserting said aligned drill guide into the lumen of said directional cannula until said drill guide engages a positive stop on said directional cannula;
  inserting a drill bit through said non-centered drill guide hole and drilling said iliac bone cavity within the iliac bone to a predetermined depth;
  removing said drill bit from a lumen of said drill guide;
  removing said drill guide from said lumen of said directional cannula;
  rotating said drill guide one hundred eighty degrees) (180°), aligning said drill guide over said directional cannula so that said non-centered drill guide hole is positioned over the sacrum;
  inserting said drill guide into said lumen of said directional cannula until said drill guide engages said positive stop on said directional cannula;
  inserting said drill bit, positioned over the sacrum, through said non-centered drill guide hole and drilling a sacrum cavity within the sacrum to a predetermined depth;
  removing said drill bit from the lumen of said drill guide;
  inserting said drill bit through a centered drill guide hole and drilling a sacroiliac joint cavity within the sacroiliac joint to a predetermined depth; and
  removing said drill bit from said lumen of said drill guide, and removing said drill guide from said lumen of said directional cannula.

14. The method of claim 13,
further comprising the steps of:
inserting a stabilization implant through said lumen of said directional cannula;
inserting an implant positioner into said lumen of said directional cannula until said implant positioner engages said implant, and a distal end of said implant engages said therapeutic cavity;
tapping a proximal end of said implant positioner until a positive stop on said directional cannula is engaged to seat said implant into said therapeutic cavity, at a predetermined depth completely within said therapeutic cavity, proportionately distributed laterally across the sacroiliac joint engaging the sacrum and the ilium;
removing said implant positioner from said lumen of said directional cannula; and
removing said directional cannula from said sacroiliac joint and said soft tissue.

* * * * *